(12) United States Patent
Boccalon et al.

(10) Patent No.: US 11,497,511 B2
(45) Date of Patent: Nov. 15, 2022

(54) ORTHOPEDIC SURGICAL INSTRUMENT INCLUDING AN ACETABULAR REAMING GUIDE

(71) Applicant: LIMACORPORATE S.P.A., Villanova di San Daniele del Friuli (IT)

(72) Inventors: Matteo Boccalon, Bicinicco (IT); Fausto Sbaiz, Codroipo (IT)

(73) Assignee: Limacorporate S.P.A., Villanova di San Daniele del Friuli (IT)

( * ) Notice: Subject to any disclaimer, the term of this patent is extended or adjusted under 35 U.S.C. 154(b) by 551 days.

(21) Appl. No.: 16/568,678

(22) Filed: Sep. 12, 2019

(65) Prior Publication Data

US 2021/0077129 A1   Mar. 18, 2021

(51) Int. Cl.
*A61B 17/17* (2006.01)
*A61B 17/16* (2006.01)
*A61B 90/00* (2016.01)
*A61B 17/88* (2006.01)
*A61B 17/00* (2006.01)

(52) U.S. Cl.
CPC ...... *A61B 17/1746* (2013.01); *A61B 17/1659* (2013.01); *A61B 17/8897* (2013.01); *A61B 90/03* (2016.02); *A61B 2017/00477* (2013.01); *A61B 2017/1602* (2013.01); *A61B 2090/034* (2016.02)

(58) Field of Classification Search
CPC .................. A61B 17/1746; A61B 17/1742
See application file for complete search history.

(56) References Cited

U.S. PATENT DOCUMENTS 8,808,302 B2 *   8/2014   Roose ............... A61B 17/1746
                                                                606/96

* cited by examiner

*Primary Examiner* — Andrew Yang
(74) *Attorney, Agent, or Firm* — Hickman Becker Bingham Ledesma LLP; Malgorzata A. Kulczycka

(57) ABSTRACT

An orthopedic surgical instrument comprising: a customized patient-specific acetabular reaming guide comprising an at least partially circular body, having an inner surface defining a slot sized to receive an acetabular reamer head, and further having a top surface defining a contact element; at least one support element configured for supporting the at least partially circular body on a patient-specific anatomy of a coxal bone; and further comprising at least one acetabular reamer head comprising a bone milling portion configured for insertion in the slot of the acetabular reaming guide; a connecting element configured for removable attachment to a reamer's shank for operation of the at least one acetabular reamer head; wherein the orthopedic surgical instrument further comprises an abutment element attached to a top portion at least one acetabular reamer head and configured to limit a milling depth of the bone milling portion, by resting on the contact element of the acetabular reaming guide.

13 Claims, 9 Drawing Sheets

ORTHOPEDIC SURGICAL INSTRUMENT INCLUDING AN ACETABULAR REAMING GUIDE

FIELD OF THE INVENTION

The present invention relates to an orthopedic surgical instrument comprising an acetabular reaming guide. In particular, the present invention pertains to customized patient-specific orthopedic surgical instruments using acetabular reamer heads available on the market. The present invention can be applied in connection with surgery for implantation of acetabular cup prostheses.

BACKGROUND

Joint arthroplasty is a surgical procedure wherein a diseased and/or damaged natural joint is replaced by a prosthetic joint. For example, in a hip arthroplasty surgical procedure, a prosthetic hip replaces a patient's natural hip. A typical prosthetic hip includes an acetabular prosthesis and a femoral prosthesis.

In preparation to total hip arthroplasty surgery (THA), an acetabular seat of a patient is milled using an acetabular reamer, in order to provide a shaped seat in the anatomy, for housing an implant portion of the acetabular prosthesis.

The milling operation with the acetabular reamer is complicated and can be performed effectively only by expert surgeons: in fact, vibrations are propagated to the reamer during milling, so that it is hard to maintain the surgical instrument in the desired position.

Moreover, bone milling shall be performed up to a determined depth, to correctly house the implant portion; if such depth is exceeded, adjacent or underlying soft tissues could be damaged.

In an ordinary operation of the acetabular reamer, milling is performed in subsequent steps starting from a reamer head with smaller diameter and then moving to reamer head(s) with larger diameter, to reach the determined size for the seat.

As aid to milling operations, acetabular reaming guides are used.

Known reaming guides are configured to maintain the reamer head in a predetermined position within the anatomy. Moreover, known reaming guides allow to perform milling up to a predetermined depth.

Document U.S. Pat. No. 8,808,302 B2 relates to a customized patient-specific acetabular orthopaedic surgical instrument; the instrument includes a customized patient-specific acetabular reaming guide including a ring-shaped body having an inner surface defining a cylindrical passageway, and a plurality of arms extending from the ring-shaped body; the guide housing may include a depth stop to limit movement of the acetabular reamer surgical tool along the longitudinal axis; a flange may secure the guide housing to the ring-shaped body.

Document U.S. Pat. No. 9,492,182 B2 relates to a customized patient-specific orthopaedic instrument for implantation of an acetabular cup prosthesis in a coxal bone of a patient; the customized patient-specific orthopaedic instrument includes acetabular reaming guide having a longitudinal passageway for an acetabular reamer and a plurality of arms with attached feet, for positioning on the coxal bone of the patient.

Document U.S. Pat. No. 9,693,785 B2 relates to a device for use in total hip arthroplasty surgery, including a first guide member having a substantially semi-circular ring having a top surface and a bottom surface, a plurality of first guide legs protruding vertically downward from the lower surface of the semi-circular ring, the first guide legs including a contact area disposed on the open end of the first guide leg; the device also includes a second guide member having an arc substantially similar to the semi-circular ring, the arc having a top surface and bottom surface, and means for connecting the second guide member to the first guide member.

Surgical instruments including acetabular reaming guides and reamers known in the art, provide for a component of a shank configured for reaching a stop with an abutment element, which is present on a handle portion of the reamer, for example a sleeve or the like.

Moreover, surgical instruments including acetabular reaming guides and reamers known in the art, provide for components which are associated to the handle portion of the acetabular reamer, which are bulky and substantially overlap with most of the acetabular reamer itself.

Therefore, instruments including acetabular reaming guides and acetabular reamers known in the art are generally bulky and may represent and obstacle, both visual and physical, for the surgeon which is impeded during the procedure.

It is an objective of the present invention to solve drawbacks of the prior art.

In particular, it is an object of the present invention to provide an instrument including an acetabular reaming guide and reamer which is improved with respect to the prior art.

SUMMARY

According to one aspect of the disclosure, it is provided an orthopedic surgical instrument comprising a customized patient-specific acetabular reaming guide comprising: an at least partially circular body, having an inner surface defining a slot sized to receive an acetabular reamer head, and further having a top surface defining a contact element, and further having at least one support element configured for supporting the at least partially circular body on a patient-specific anatomy of a coxal bone. The orthopedic surgical instrument further comprises at least one acetabular reamer head comprising a bone milling portion configured for insertion in the slot of the acetabular reaming guide, a connecting element configured for removable attachment to a reamer's shank for operation of the at least one acetabular reamer head. The orthopedic surgical instrument further comprises an abutment element attached to a top portion at least one acetabular reamer head and configured to limit a milling depth of the bone milling portion, by resting on the contact element of the acetabular reaming guide.

According to another aspect of the disclosure, it is provided an orthopedic surgical instrument comprising a customized patient-specific acetabular reaming guide comprising an at least partially circular body, and further comprising an abutment element configured to limit a milling depth of a bone milling portion of an acetabular reamer head, wherein said abutment element is a ring-like element with outward tapering configured to match with a corresponding surface of the acetabular reaming guide.

According to yet another aspect of the disclosure, it is provided an orthopedic surgical instrument comprising a customized patient-specific acetabular reaming guide comprising an at least partially circular body, and further comprising at least one acetabular reamer head comprising: a bone milling portion configured for insertion in the at least partially circular body of the acetabular reaming guide and defining a hollow hemispherical body, a connecting element configured for removable attachment to a reamer's shank for operation of the at least one acetabular reamer head, and an abutment element configured to limit a milling depth of the bone milling portion, by resting on the at least partially circular body of the acetabular reaming guide.

Advantageously, the orthopedic surgical instrument according to the invention comprises an acetabular reaming guide and an abutment element which are improved over the prior art.

In particular, for example, the acetabular reaming guide and the abutment element are generally more compact and do not hinder vision or action of a surgeon during a surgical procedure.

Other features and advantages of the invention will be apparent from the following description of preferred embodiments, and from the claims.

BRIEF DESCRIPTION OF THE DRAWINGS

The skilled in the art will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present invention is directed to an orthopedic surgical instrument, in particular used in connection with surgery for implantation of acetabular cup prostheses.

Figure 1:
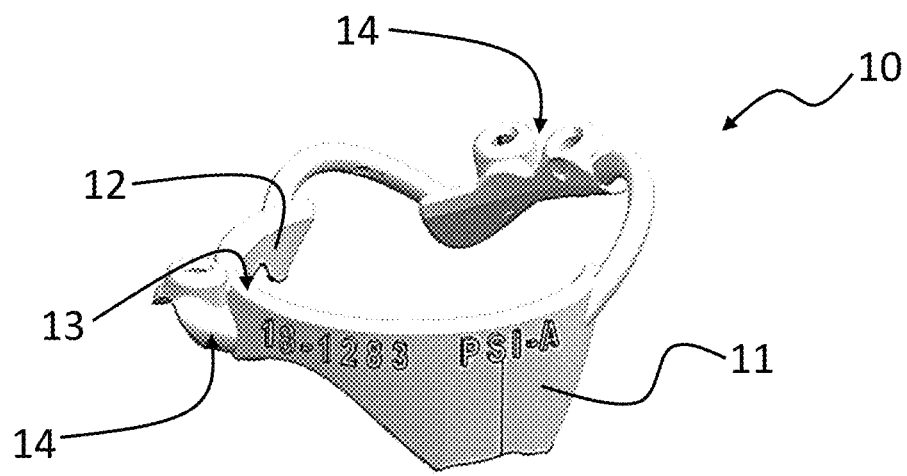
FIG. 1 shows an implementation of acetabular reaming guide according to the invention.

FIG. 1 shows an implementation of acetabular reaming guide 10 according to the invention.

The acetabular reaming guide 10 has an at least partially circular body 11, having an inner surface 12 defining a slot sized to receive an acetabular reamer head.

The acetabular reaming guide 10 further has a top surface 13 defining a contact element which will be further described.

The acetabular reaming guide 10 further has at least one or a plurality of support elements 14, which are configured for supporting the at least partially circular body 11 on a patient-specific anatomy of a coxal bone. These support elements 14 may be flanges, or supporting legs, or the like.

Figure 2:
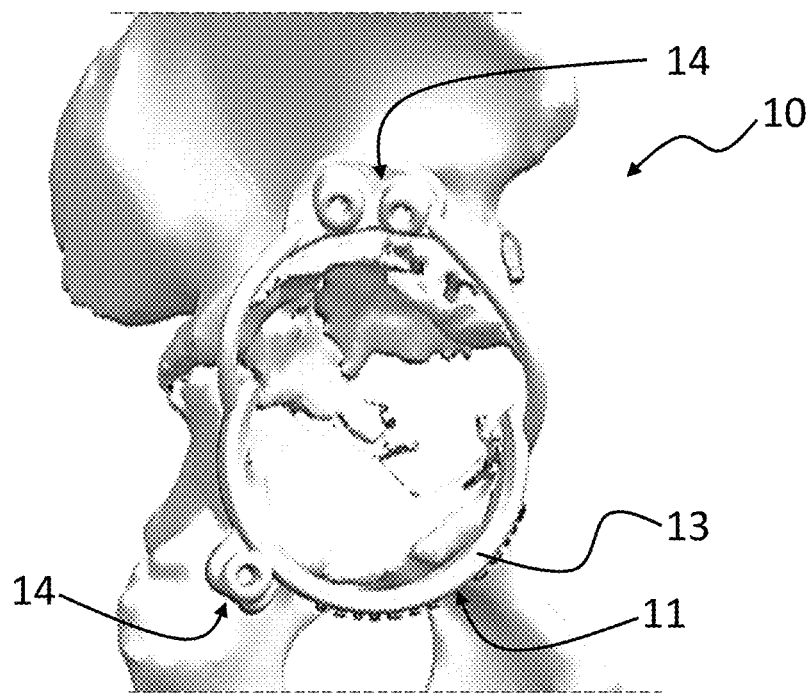
FIG. 2 shows the acetabular reaming guide of FIG. 1 placed on a coxal bone.

FIG. 2 shows the acetabular reaming guide 10 placed on a coxal bone of a patient. The acetabular reaming guide 10 is a customized patient-specific element.

The acetabular reaming guide 10 is configured for being positioned on a patient's anatomy, in particular associated to an acetabular seat of a coxal bone.

In some implementations, the support elements may have the same layout and sizes of the elements which will be used for permanent fixation of the prosthesis.

In some implementations, the acetabular reaming guide may be removably associated to the patient's anatomy by means of pins, screws, or Kirschner wires (K-wires).

In some implementations, the one or more Kirschner wires (K-wires) may be used for guiding the association between the acetabular reaming guide and the anatomy.

Figure 3A:
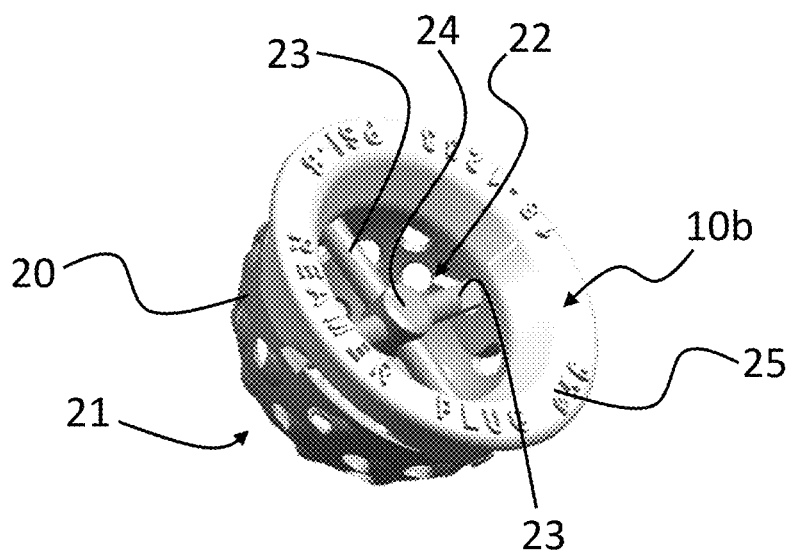
FIGS. 3A and 3B shows an implementation of acetabular reamer head according to the invention.

FIG. 3A shows an implementation of acetabular reamer head 20 according to the invention.

The acetabular reamer head 20 comprises a bone milling portion 21 configured for insertion in the slot of the acetabular reaming guide 10. The bone milling portion 21 defines a hollow hemispherical shape.

The acetabular reamer head 20 further comprises a connecting element 22, configured for removable attachment to a reamer's shank (not shown) for operation of the at least one acetabular reamer head 20.

In an implementation, the connecting element comprises a pair of straight hooking elements 23, orthogonally disposed around a central pin connection 24.

The acetabular reaming guide 10 is configured for association with a second element 10b, as it will be further described.

In an implementation, a reamer's shank can be attached to the connecting element 22. In particular, the reamer's shank passes inside and through the ring-like abutment element 25 of the second element 10b, for attachment on the connecting element 22 of the acetabular reamer head 20.

Figure 3B:
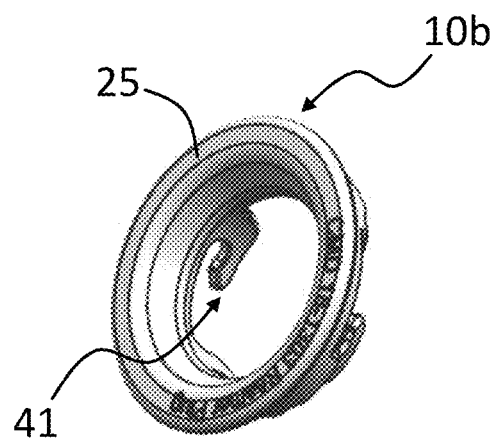

FIG. 3B shows an implementation of a second element 10b according to the invention.

The second element 10b comprises a gripping member 41, configured to be attachable/detachable to the acetabular reamer head 20.

In an implementation, the gripping member comprises at least one hooking element 41 configured to be attachable/detachable to the connecting element 22 of the acetabular reamer head 20.

In an implementation, the second element 10b can be attached to the acetabular reamer head 20 by insertion and subsequent rotation, preferably counter-clockwise.

The second element 10b comprises an abutment element 25 configured to limit a milling depth of the bone milling portion.

In an implementation, the abutment element 25 is a ring-like element with outward tapering.

Figure 4:
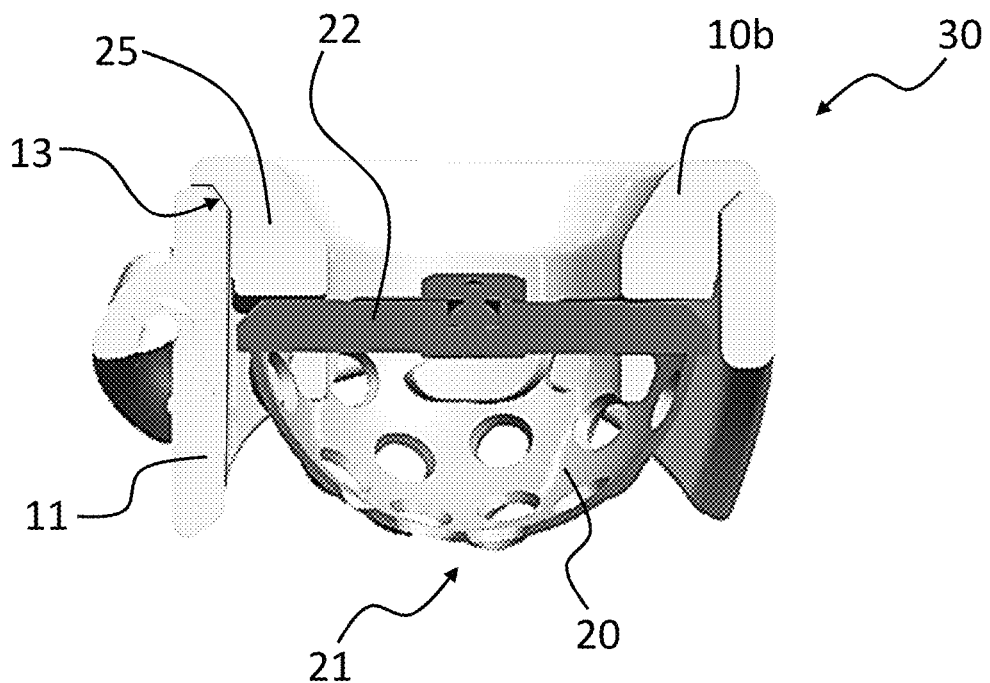
FIG. 4 shows a cut-out view of an implementation of orthopedic surgical instrument according to the invention.

FIG. 4 shows a cut-out view of an orthopedic surgical instrument 30 according to the invention.

In an implementation, the orthopedic surgical instrument 30 comprises the customized patient-specific acetabular reaming guide 10 and the acetabular reamer head 20.

According to a variant implementation, not shown, the second element 10b may be integrally made with the acetabular reamer head 20.

The abutment element 25 is configured to limit a milling depth of the bone milling portion, by resting on the contact element 13 of the acetabular reaming guide 10. In particular, the abutment element 25 is configured to match with a corresponding surface of the contact element 13.

The acetabular reamer head 20 can proceed with the milling operation up to a desired milling depth. The milling depth is selectable by varying the size of the contact element 13 in the acetabular reaming guide 10 and/or by varying the size of the abutment element 25 in the second element 10b.

In particular, the ring-like abutment element 25 has a longitudinal height which is less than its radius size. In that, the overall volume of the orthopedic surgical instrument 30, and the volume of the acetabular reamer head 20, is reduced, so that the surgeon has better view and access to the surgery area.

Moreover, the reduced and simple structure of the orthopedic surgical instrument 30 makes it for a reduced production cost.

Figure 5:
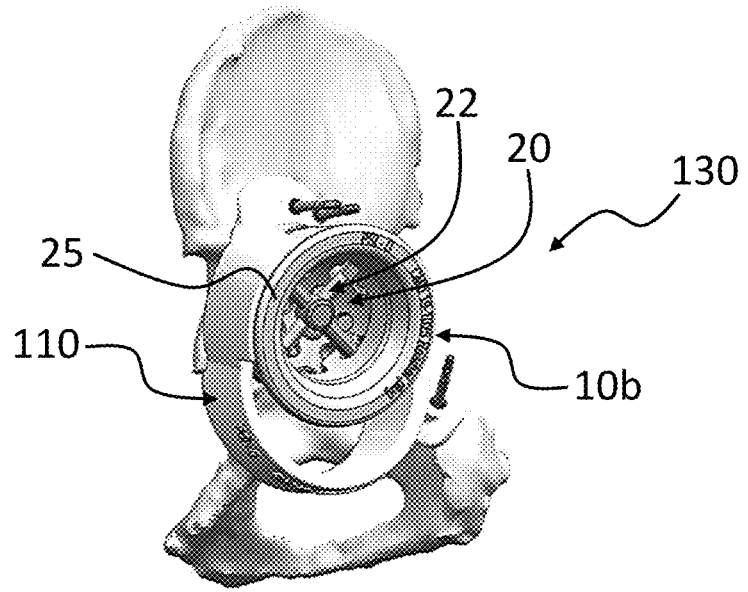
FIG. 5 shows an implementation of orthopedic surgical instrument according to the invention, on a coxal bone.

FIG. 5 shows an implementation of orthopedic surgical instrument 130 on a coxal bone.

The orthopedic surgical instrument 130 comprises a customized patient-specific acetabular reaming guide 110, comprising an at least partially circular body The orthopedic surgical instrument 130 further comprises an abutment element 25 configured to limit a milling depth of the bone milling portion.

The abutment element 25 is a ring-like element, with outward tapering configured to match with a corresponding surface of the acetabular reaming guide 110. The ring-like element 25 has a longitudinal height which is less than its radius size. The orthopedic surgical instrument 130 further comprises a acetabular reamer head 20, comprising a bone milling portion configured for insertion in the at least partially circular body of the acetabular reaming guide 110, a connecting element 22 configured for removable attachment to a reamer's shank for operation of the at least one acetabular reamer head 20.

Figure 6:
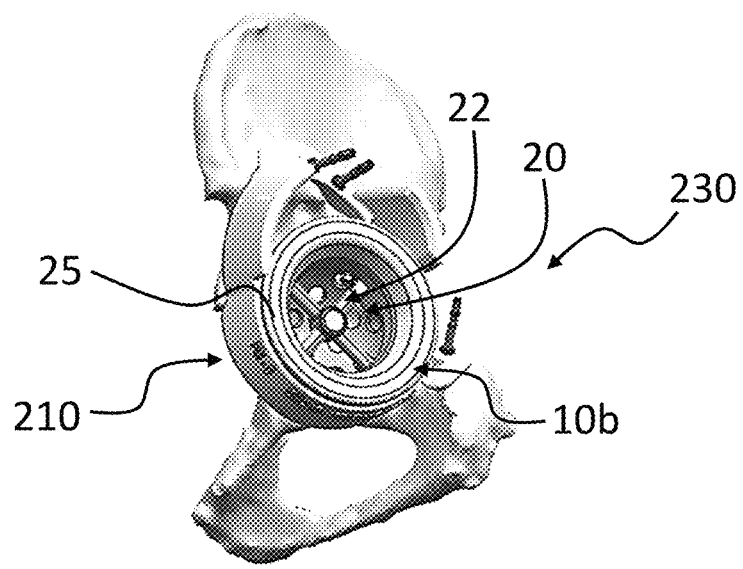
FIG. 6 shows a further implementation of orthopedic surgical instrument according to the invention, on a coxal bone.

FIG. 6 shows a further implementation of orthopedic surgical instrument 230 on a coxal bone.

The orthopedic surgical instrument 230 comprises a customized patient-specific acetabular reaming guide 210, comprising an at least partially circular body The orthopedic surgical instrument 230 further comprises an abutment element 25 configured to limit a milling depth of the bone milling portion.

The abutment element 25 is a ring-like element, with outward tapering configured to match with a corresponding surface of the acetabular reaming guide 210. The ring-like element 25 has a longitudinal height which is less than its radius size.

The orthopedic surgical instrument 230 further comprises a acetabular reamer head 20, comprising a bone milling portion configured for insertion in the at least partially circular body of the acetabular reaming guide 210, a connecting element 22 configured for removable attachment to a reamer's shank for operation of the at least one acetabular reamer head 20.

Considering the orthopedic surgical instrument 130 and the orthopedic surgical instrument 230, it is clear that a same acetabular reamer head 20 can be associated to any suitably shaped acetabular reaming guide according to the invention.

In an implementation, the acetabular reaming guide is configured to allow one or more milling passes, by a same acetabular reamer or by a plurality of acetabular reamers of different sizes. For example, the acetabular reaming guide may include two or more contact elements which would be suitable for abutment with a respective plurality of differently sized abutment elements of acetabular reamers.

In an implementation, an orthopedic surgical instrument comprises a plurality of acetabular reamer heads, comprising a respective plurality of bone milling portions of different sizes. In agreement with this implementation, a respective plurality of abutment elements is configured to match with a corresponding surface of the acetabular reaming guide, so as to appropriately control milling depth.

Figure 7:
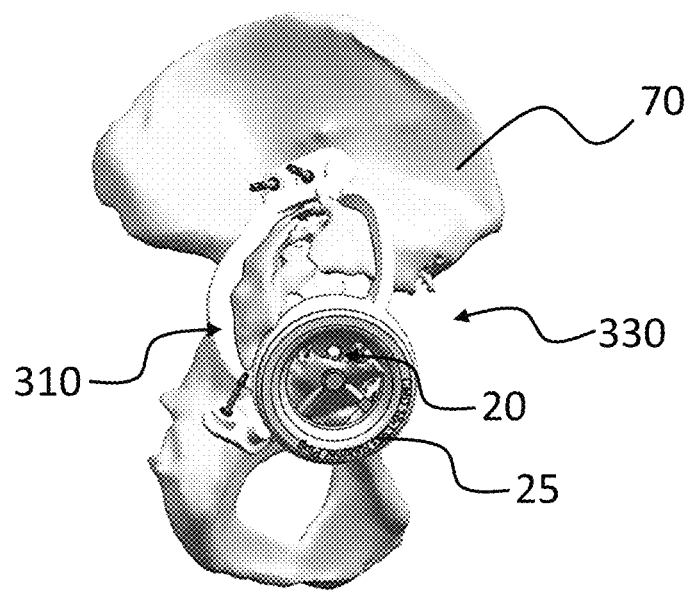
FIG. 7 shows a yet further implementation of orthopedic surgical instrument according to the invention, on a coxal bone.

FIG. 7 shows a yet further implementation of orthopedic surgical instrument 330, on a coxal bone.

The orthopedic surgical instrument 330 comprises an acetabular reaming guide 310, which is a customized patient-specific guide.

The orthopedic surgical instrument 330 further comprises an acetabular reamer head 20.

The orthopedic surgical instrument 330 further comprises an abutment element 25 configured to limit a milling depth of the bone milling portion.

The abutment element 25 is a ring-like element, with outward tapering configured to match with a corresponding surface of the acetabular reaming guide 310. The ring-like element 25 has a longitudinal height which is less than its radius size.

In an implementation, the acetabular reaming guide 310 is configured for guiding the at least one acetabular reamer head 20 in a milling procedure of a portion of pelvis bone 70.

Figure 8A:
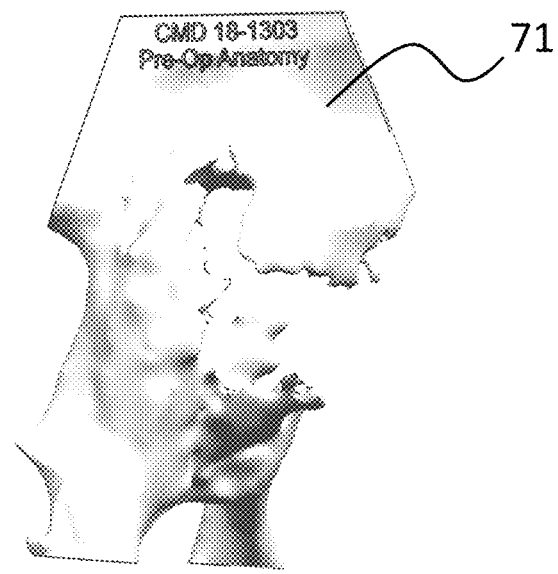
FIGS. 8A and 8B respectively show artificial anatomies corresponding to the anatomy of the coxal bone of FIG. 7, prior and following a bone removal operation.
Figure 8B:
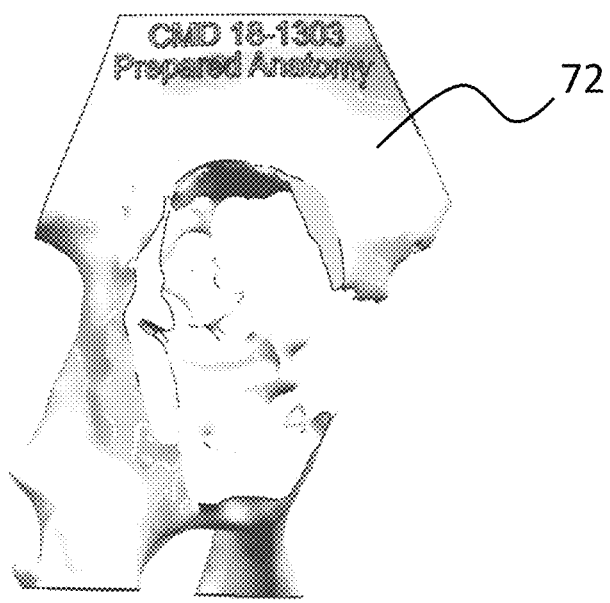

FIGS. 8A and 8B respectively show a first artificial anatomy 71 and a second artificial anatomy 72 corresponding to the anatomy of the coxal bone 70 of FIG. 7 prior and following the bone removal operation.

As previously mentioned, the acetabular reaming guide 310 is designed ad manufactured according to the specifics of the coxal bone 70, being a customized patient-specific acetabular reaming guide.

In an implementation, the acetabular reaming guide 310 is placed on the first artificial anatomy 71 prior to implantation on the coxal bone 70, in a trial step before surgery.

The second artificial anatomy 72 may be used as a comparison reference as to identify if enough bone reaming has been performed on the coxal bone.

Furthermore, the second artificial anatomy 72 may be used to assess the positioning of an implant and/or trial implant in the reaming area.

In an implementation, see FIG. 7, the acetabular reaming guide 310 is configured as a cutting guide to perform a bone removal of a portion of the coxal bone, e.g. the bone removal of sclerotic bone.

According to this implementation, the second artificial anatomy 72 may be used as a comparison reference as to identify if enough bone cut has been performed on the coxal bone.

Figure 9:
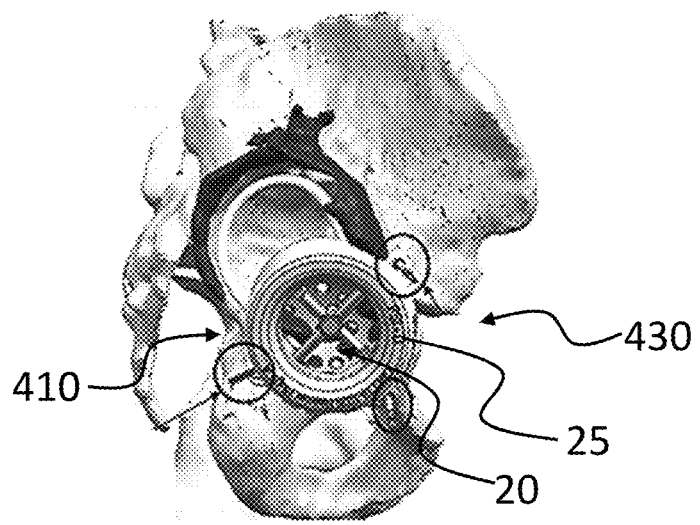
FIG. 9 shows a yet further implementation of orthopedic surgical instrument according to the invention, on a coxal bone.

FIG. 9 shows a yet further implementation of orthopedic surgical instrument 430 according to the invention, on a coxal bone. The orthopedic surgical instrument 430 comprises an acetabular reaming guide 410.

In an implementation, the acetabular reaming guide 410 is further configured for guiding a removal of osteophytes (dark textured in FIG. 9) from the anatomy.

Figure 10:
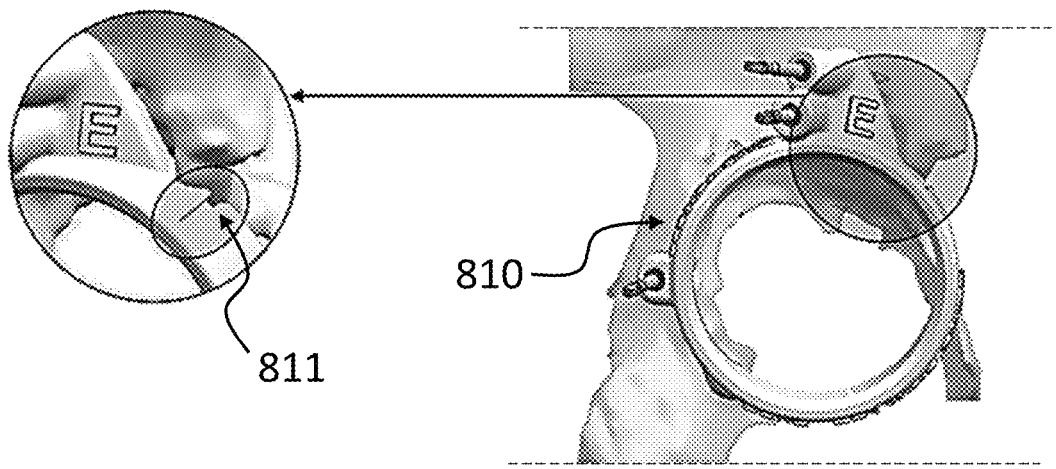
FIG. 10 shows a detail of an implementation of acetabular reaming guide according to the invention.

FIG. 10 shows a detail of an implementation of acetabular reaming guide 810.

In an implementation, the acetabular reaming guide 810 comprises one or more reference notches 811 which are configured for locating a preferred position on the patient-specific anatomy of the coxal bone.

In particular, the reference notches 811 are configured as an anatomical landmark.

In an implementation, a reference notch 811 is meant as a reference between the flange of the acetabular reaming guide 810 and an anterior iliac crest of a coxal bone, in order to guide the positioning of the acetabular reaming guide 810.

Figure 11:
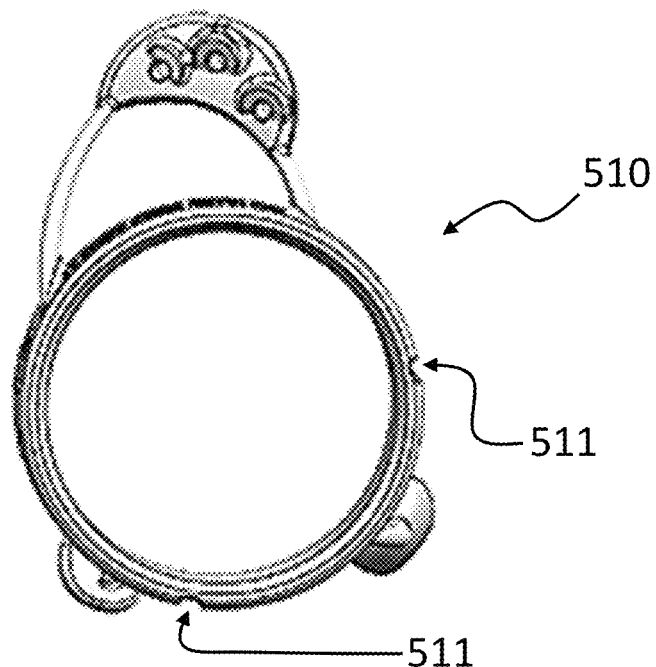
FIG. 11 shows a yet further implementation of acetabular reaming guide according to the invention.

FIG. 11 shows a yet further implementation of acetabular reaming guide 510.

The reaming guide 510 comprises an at least partially circular body, having an inner surface defining a slot sized to receive an acetabular reamer head, and further having a top surface defining a contact element.

The reaming guide 510 further comprises at least one support element configured for supporting the at least partially circular body on a patient-specific anatomy of a coxal bone.

In an implementation, the acetabular reaming guide 510 comprises a plurality of cutting notches 511, configured for aiding in cutting of the at least partially circular body to a smaller circular length, thereby reducing the size of the acetabular reaming guide 510 for implantation if the surgeon considers it necessary.

Figure 12:
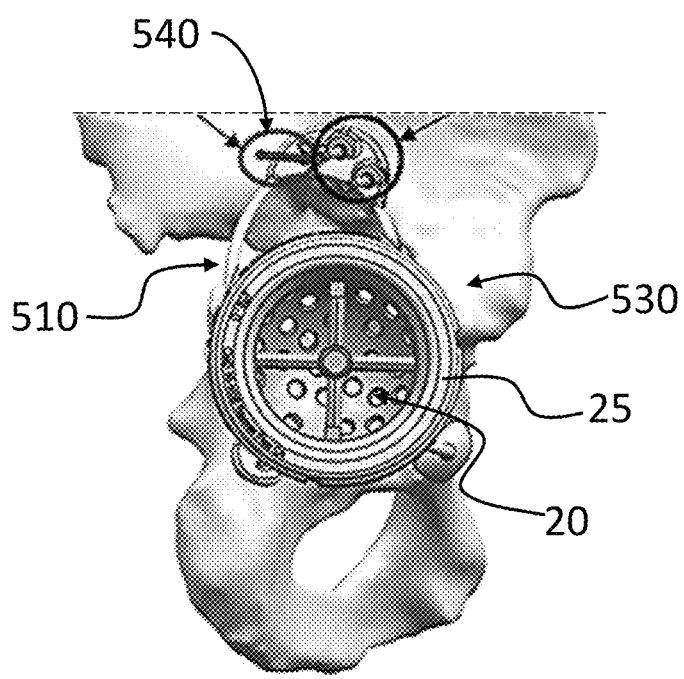
FIG. 12 shows an implementation of orthopedic surgical instrument according to the invention including the acetabular reaming guide of FIG. 11.

FIG. 12 shows an implementation of orthopedic surgical instrument 530.

The orthopedic surgical instrument 530 comprises a customized patient-specific acetabular reaming guide 510 comprising an at least partially circular body The orthopedic surgical instrument 530 further comprises an abutment element 25 configured to limit a milling depth of the bone milling portion, by resting on the at least partially circular body of the acetabular reaming guide 510.

The orthopedic surgical instrument 530 further comprises at least one acetabular reamer head 20.

The acetabular reamer head 20 comprises a bone milling portion configured for insertion in the at least partially circular body of the acetabular reaming guide and defining a hollow hemispherical body.

The acetabular reamer head 20 further comprises a pair of straight hooking elements associated to the hollow hemispherical body and configured for removable attachment to a reamer's shank for operation of the at least one acetabular reamer head. Preferably, the pair of straight hooking elements are orthogonally disposed around a central pin connection.

In some implementations, a Kirschner wire (K-wire) may be used for guiding the association between one or more acetabular reaming guides and the anatomy.

Figure 13:
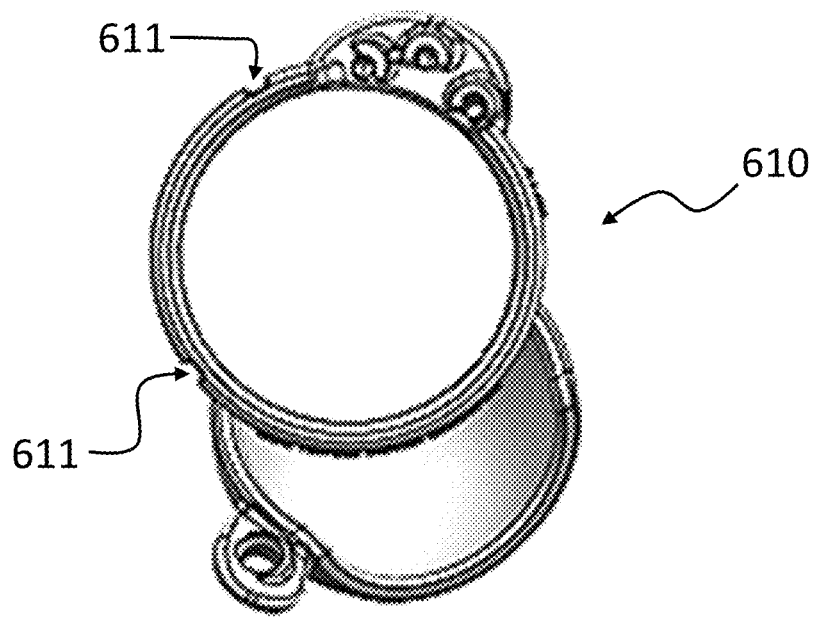
FIG. 13 shows a yet further implementation of acetabular reaming guide according to the invention.

FIG. 13 shows a yet further implementation of acetabular reaming guide 610.

The reaming guide 610 comprises an at least partially circular body, having an inner surface defining a slot sized to receive an acetabular reamer head, and further having a top surface defining a contact element.

The reaming guide 610 further comprises at least one support element configured for supporting the at least partially circular body on a patient-specific anatomy of a coxal bone.

Figure 14:
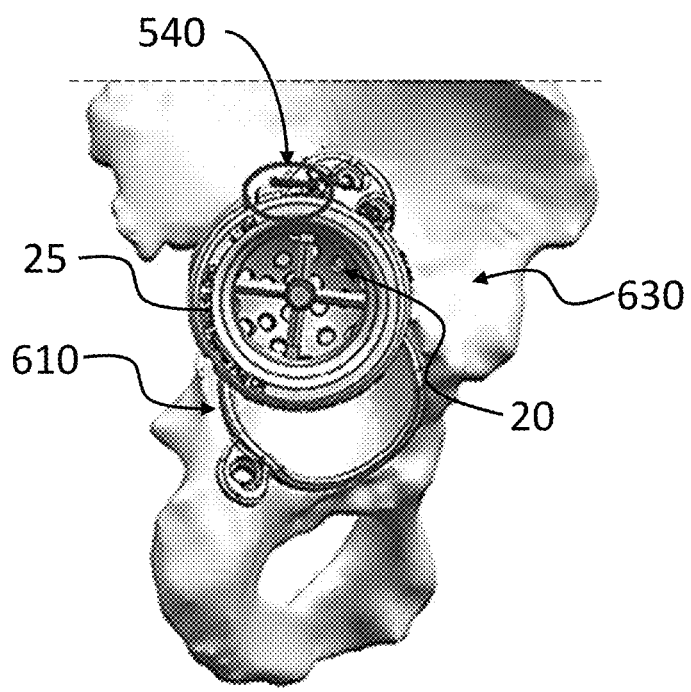
FIG. 14 shows an implementation of orthopedic surgical instrument according to the invention including the acetabular reaming guide of FIG. 13.

In an implementation, the acetabular reaming guide 610 comprises a plurality of cutting notches 611, configured for aiding in cutting the at least partially circular body to a smaller circular length, thereby reducing the size of the acetabular reaming guide 610 for implantation FIG. 14 shows an implementation of orthopedic surgical instrument 630.

The orthopedic surgical instrument 630 comprises a customized patient-specific acetabular reaming guide 610 comprising an at least partially circular body.

The orthopedic surgical instrument 630 further comprises an abutment element 25 configured to limit a milling depth of the bone milling portion, by resting on the at least partially circular body of the acetabular reaming guide 610.

The orthopedic surgical instrument 630 further comprises at least one acetabular reamer head 20.

The acetabular reamer head 20 comprises a bone milling portion configured for insertion in the at least partially circular body of the acetabular reaming guide and defining a hollow hemispherical body.

The acetabular reamer head 20 further comprises a pair of straight hooking elements associated to the hollow hemispherical body and configured for removable attachment to a reamer's shank for operation of the at least one acetabular reamer head. Preferably, the pair of straight hooking elements are orthogonally disposed around a central pin connection.

The acetabular reamer head 20 further comprises an abutment element configured to limit a milling depth of the bone milling portion, by resting on the at least partially circular body of the acetabular reaming guide.

In some implementations, a Kirschner wire (K-wire) 540 may be used for guiding the association between two or more acetabular reaming guides and the anatomy.

In particular, see FIGS. 12 and 14, the same K-wire 540 may be used as reference for the positioning of a first acetabular reaming guide 510.

Following a first reaming, the first acetabular reaming guide 510 is then removed, keeping the K-wire guide 540 in position. The second acetabular reaming guide 610 is then placed with reference to the same K-wire guide 540 in order to perform a second reaming at a different position on the coxal bone.

Figure 15:
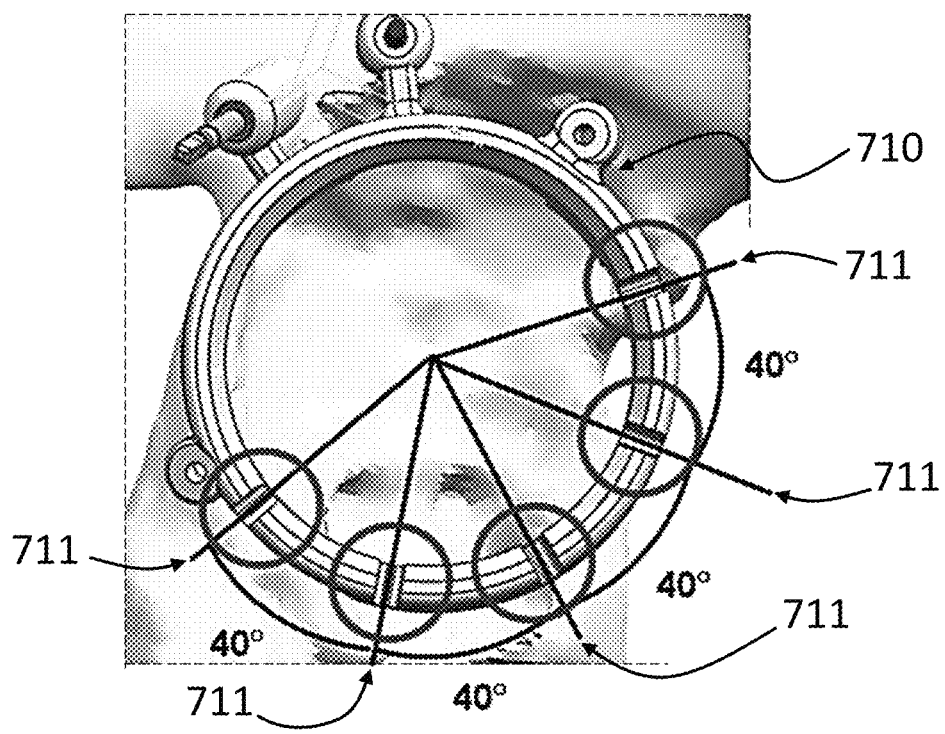
FIG. 15 shows a yet further implementation of acetabular reaming guide according to the invention.

FIG. 15 shows a yet further implementation of acetabular reaming guide 710.

In an implementation, the acetabular reaming guide 710 comprises a plurality of cutting notches 711, configured for aiding in cutting of the at least partially circular body to a smaller circular length, thereby reducing the size of the acetabular reaming guide 710 for implantation. Preferably, the acetabular reaming guide 701 comprises two or more cutting notches 711, which are angularly spaced in an even manner over the circular body of the acetabular reaming guide 710.

If necessary, especially for allowing the insertion of the acetabular reaming guide 710, the cutting slots provided by the cutting notches 711 can be used to cut the inferior half of the acetabular reaming guide 710.

Although the present invention has been described in considerable detail with reference to certain preferred embodiments thereof, other variants may become apparent to those skilled in the art who consider the present description.

Therefore, the disclosed preferred embodiments are provided primarily for illustrative purposes and are not meant as limiting the present invention.

The invention claimed is:

1. An orthopedic surgical instrument comprising:
   a customized patient-specific acetabular reaming guide comprising:
     an at least partially circular body, having an inner surface defining a slot sized to receive an acetabular reamer head, and further having a top surface defining a contact element, and
     at least one support element configured for supporting the at least partially circular body on a patient-specific anatomy of a coxal bone;
   and further comprising at least one acetabular reamer head comprising:
     a bone milling portion configured for insertion in the slot of the acetabular reaming guide,
     a connecting element configured for removable attachment to a reamer's shank for operation of the at least one acetabular reamer head,
   wherein the orthopedic surgical instrument further comprises
     an abutment element attached to a top portion at least one acetabular reamer head and configured to limit a milling depth of the bone milling portion, by resting on the contact element of the acetabular reaming guide,
   wherein the abutment element is attached to the top portion of the at least one acetabular reamer head, opposite to the bone milling portion and surrounding the connecting element.

2. The orthopedic surgical instrument of claim 1, wherein the abutment element comprises a gripping member configured to be attachable to/detachable from the acetabular reamer head.

3. The orthopedic surgical instrument of claim 1, wherein said abutment element is a ring-like element with outward tapering, configured to match with a corresponding surface of the contact element.

4. The orthopedic surgical instrument of claim 3, wherein the ring-like element has a longitudinal height which is less than its radius size.

5. The orthopedic surgical instrument of claim 3, wherein the connecting element is attachable by the reamer's shank, passing through the ring-like abutment element.

6. The orthopedic surgical instrument of claim 1, comprising a plurality of acetabular reamer heads, comprising a respective plurality of bone milling portions of different sizes.

7. The orthopedic surgical instrument of claim 1, wherein the acetabular reaming guide comprises one or more reference notches, configured for locating a preferred position on the patient-specific anatomy of the coxal bone.

8. The orthopedic surgical instrument of claim 1, wherein the acetabular reaming guide comprises a plurality of cutting notches, configured for cutting the at least partially circular body to a smaller circular length, thereby reducing the size of the acetabular reaming guide for implantation.

9. The orthopedic surgical instrument of claim 1, wherein the acetabular reaming guide is configured for guiding the at least one acetabular reamer head in a milling procedure of a pelvis' bone portion.

10. The orthopedic surgical instrument of claim 1, wherein the acetabular reaming guide is further configured for guiding a removal of osteophytes.

11. An orthopedic surgical instrument comprising:
    a customized patient-specific acetabular reaming guide comprising an at least partially circular body;
    and further comprising an abutment element configured to limit a milling depth of a bone milling portion of an acetabular reamer head, wherein said abutment element is a ring-like element with outward tapering configured to match with a corresponding surface of the acetabular reaming guide.

12. The orthopedic surgical instrument of claim 11, wherein the ring-like element has a longitudinal height which is less than its radius size.

13. An orthopedic surgical instrument comprising:
    a customized patient-specific acetabular reaming guide comprising an at least partially circular body;
    and further comprising at least one acetabular reamer head comprising:
      a bone milling portion configured for insertion in the at least partially circular body of the acetabular reaming guide and defining a hollow hemispherical body,
      a connecting element configured for removable attachment to a reamer's shank for operation of the at least one acetabular reamer head;
    and further comprising an abutment element configured to limit a milling depth of the bone milling portion, by resting on the at least partially circular body of the acetabular reaming guide,
    wherein the abutment element comprises a gripping member configured to be attachable to/detachable from the at least one acetabular reamer head.

* * * * *